(12) United States Patent
Platt

(10) Patent No.: US 9,700,360 B2
(45) Date of Patent: Jul. 11, 2017

(54) CHANNELED BONE PLATE AND METHODS FOR IMPLANTING THE SAME

(71) Applicant: James Platt, Apollo Beach, FL (US)

(72) Inventor: James Platt, Apollo Beach, FL (US)

( * ) Notice: Subject to any disclaimer, the term of this patent is extended or adjusted under 35 U.S.C. 154(b) by 317 days.

(21) Appl. No.: 14/304,661

(22) Filed: Jun. 13, 2014

(65) Prior Publication Data

US 2014/0371798 A1    Dec. 18, 2014

Related U.S. Application Data

(60) Provisional application No. 61/834,820, filed on Jun. 13, 2013.

(51) Int. Cl.
*A61B 17/82*    (2006.01)
*A61B 17/80*    (2006.01)
*A61B 17/88*    (2006.01)

(52) U.S. Cl.
CPC ............. *A61B 17/80* (2013.01); *A61B 17/82* (2013.01); *A61B 17/8866* (2013.01)

(58) Field of Classification Search
CPC ...... A61B 17/82; A61B 17/823; A61B 17/826
USPC ........................................ 606/280–299, 74
See application file for complete search history.

(56) References Cited

U.S. PATENT DOCUMENTS

| | | | | |
|---|---|---|---|---|
| 6,017,347 A * | 1/2000 | Huebner | ............... | A61B 17/82 606/103 |
| 6,093,201 A * | 7/2000 | Cooper | ............... | A61B 17/80 606/232 |
| 8,267,973 B2 * | 9/2012 | Humphrey | ............... | A61B 17/0401 606/232 |
| 8,926,675 B2 * | 1/2015 | Leung | ............... | A61B 17/80 606/291 |
| 2006/0241617 A1 * | 10/2006 | Holloway | ............... | A61B 17/80 606/70 |
| 2006/0264947 A1 * | 11/2006 | Orbay | ............... | A61B 17/1615 606/291 |
| 2007/0093835 A1 * | 4/2007 | Orbay | ............... | A61B 17/8061 606/291 |
| 2011/0004252 A1 * | 1/2011 | Velikov | ............... | A61B 17/80 606/280 |
| 2014/0128921 A1 * | 5/2014 | Parsons | ............... | A61B 17/8061 606/281 |

OTHER PUBLICATIONS

Zimmer, NCB Periprosthetic Femur Plate System, Catalog, 2010, pp. 1-6, Zimmer, Inc., USA.

* cited by examiner

*Primary Examiner* — Matthew Lawson
(74) *Attorney, Agent, or Firm* — Lowry Blixseth LLP; Scott M. Lowry

(57) ABSTRACT

The channeled bone plate includes a substantially rigid and elongated member for use in stabilizing and splinting fractured sections of a broken bone. This elongated member includes a bottom surface and a top surface, with at least one transverse channel formed from the bottom surface. The transverse channel has a size and shape to at least partially accommodate selective insertion of a cable to permit flush mounting of the bottom surface of the elongated member to the fractured sections of the broken bone simultaneously with flush wrapping of the cable around an external surface of the fractured sections of the broken bone. The elongated member and the cable cooperate to support the broken bone as an implant splint.

8 Claims, 6 Drawing Sheets

Fig. 13
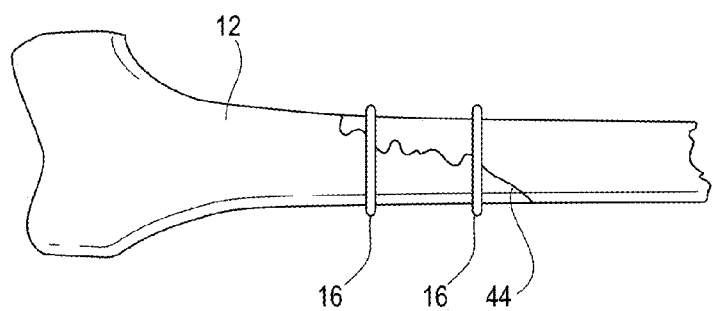
Fig. 14
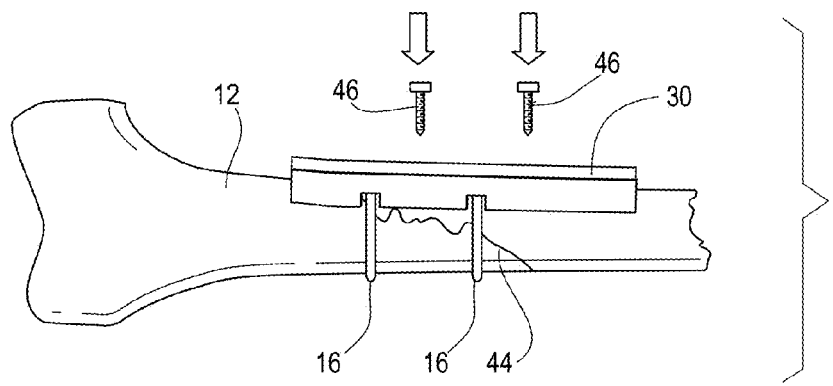
Fig. 15
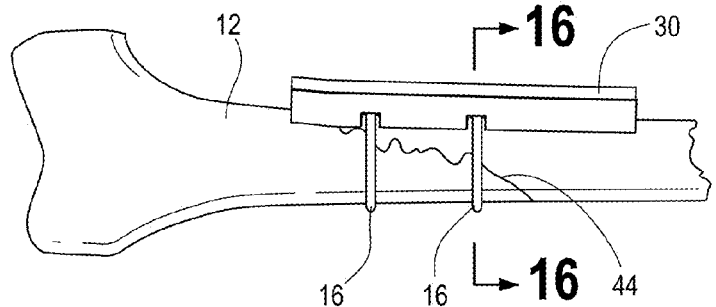
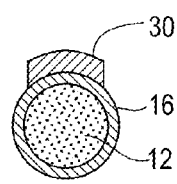
Fig. 16

CHANNELED BONE PLATE AND METHODS FOR IMPLANTING THE SAME

BACKGROUND OF THE INVENTION

The present invention generally relates to a channeled bone plate and related methods for implanting the same for use in repairing bone fractures. More specifically, the present invention relates to a bone plate including one or more channels that permit flush mounting of wires or cables around a fractured bone as part of splinting fractured sections of a broken bone.

Open reduction with internal fixation (ORIF) has long been a method for repairing severe long bone fractures in orthopedic surgery. Typically, a long intramedullary rod or bone plate is used to stabilize the fracture once it is reduced. Without proper reduction, a high percentage of fractures fail to properly heal. That is, fractured sections of the bone may not properly grow back together in proper alignment.

Temporary clamps, pins, and/or cables are typically used to achieve proper reduction and to hold two sides of a severe long bone fracture together to allow the bone plate to be implanted. The bone plate acts as a buttress or brace to hold the fractured bone in the proper orientation, which in turn encourages proper aligned healing and fusion of the fractured bone. Clamps are typically used initially to hold the fracture together. Unfortunately, clamps cannot be used alone for reduction because the shape of the clamp interferes with proper implantation of the bone plate. More specifically, the surgical opening through which an ORIF procedure is performed exposes only a small portion of the fractured bone. To hold the fractured bone in proper alignment, the clamp must cover a large portion of the exposed bone. The bone plate cannot be implanted because the clamp is in the way. Alternatively, temporary pins can be inserted away from the location where the bone plate will be implanted to provide added support in conjunction with the clamps while preventing interference with bone plate implantation. The pins may stabilize the fracture enough to remove the clamps to allow for attachment of the bone plate via a series of screws that insert into and threadingly engage the bone.

Unfortunately, the pins are not suitable for use in certain fracture patterns. For example, in periprosthetic fractures (e.g., as shown in FIG. 1) that occur around previously implanted orthopedic devices (e.g., total knee or hip replacements) require cables or wires to hold pieces of the fractured bone together. These cables or wires are typically between 1.02 millimeters (18 gauge wire) and 2.0 millimeters in diameter. Once the wires stabilize the fractured bone, a bone plate is placed on top of the cables and screwed into the bone. It is preferable that the cables or wires remain wrapped around the bone after bone plate implantation since the cables or wires aid the bone plate in bracing and supporting the fractured bone. Although, the cables or wires may be removed while the screws in the bone plate are tightened so that the bone plate more securely seats flush with the bone, otherwise the bone plate may be biased away from the bone by an approximate width of the wire or cable wrapped around fractured portions of the fractured bone. If the bone plate does not remain flush during the healing process, the bone may become misaligned and improperly heal.

Two devices are known in the prior art that facilitate bone plate implantation for purposes of setting severe long bone fractures. One prior art solution is shown in FIG. 2 and includes a buttoned bone plate 10 that couples to a fractured bone 12 through use of a button 14 that permits slidethrough mounting of a cable 16. The button 14 threadingly attaches to a top surface 18 of the buttoned bone plate 10 and contains a through-hole 20 to permit slide through engagement of the cable 16. To implant, the buttoned bone plate 10 is placed on top of the fractured bone 12 and the cable 16 is routed through the through-hole 20 and around both the buttoned bone plate 10 and the bone 12. The drawback of this device is that a gap 22 exists between the bone 12 and the cable 16 since the cable 16 wraps around both the buttoned bone plate 10 and the bone 12. The gap 22 reduces the ability of the cable 16 to snugly hold the two fragments of the bone 12 in the proper position. This may, in turn, lead to misalignment of the bone 12 and improper healing.

The other prior art solution shown in FIGS. 3 and 4 is a tunneled bone plate 24 that includes one or more tunnels 26 that permit slide-through mounting of the cables 16 to the tunneled bone plate 24, in much the same way as the button 14. The tunnels 26 extend through the width of the tunneled bone plate 24 and are generally parallel to the top surface 18. In this solution, the cable 16 routes through the width of the plate 24 via the tunnels 26 as shown in FIGS. 3 and 4, as opposed to being connected to the top surface 18 of the buttoned bone plate 10 via the button 14, as in shown in FIG. 2. Threading the cable 16 through the tunneled bone plate 24 in the manner shown generally in FIGS. 3 and 4 prevent the cable 16 from sitting flush against the fractured bone 12, thereby also creating a gap 28 between the bone 12 and the cable 16. While this gap 28 may be smaller than the gap 22 shown in FIG. 2 with respect to the buttoned bone plate 10, the gap 28 is still large enough to permit undesired relative movement of fractured sections of bone, which can lead misalignment. Thus, the buttoned bone plate 10 and the tunneled bone plate 24 are insufficient solutions to adequately maintain fractured sections of bone in preferred alignment to facilitate proper healing.

There exists, therefore, a significant need in the art for a channeled bone plate and methods for implanting the same that permits flush mounting of one or more cables or wires designed to wrap around and secure fractured sections of a bone underneath the bone plate, while simultaneously permitting the bone plate to sit flush against fractured bone sections substantially along its length, thereby substantially eliminating the undesirable gap that exists between the wrapped cables or wires and fractured bone that permits movement of relative sections of the bone fracture. The present invention fulfills these needs and provides further related advantages.

SUMMARY OF THE INVENTION

The channeled bone plate disclosed herein includes a substantially rigid and elongated member for use in stabilizing and splinting fractured sections of a broken bone. The elongated member generally includes a top surface, and a bottom surface having at least one transverse channel formed therein. The transverse channel preferably has a size and shape to at least partially accommodate selective insertion of a cable to permit flush mounting of the bottom surface of the elongated member to the fractured sections of the broken bone simultaneously with flush wrapping of the cable around an external surface of the fractured sections of the broken bone. This feature, unlike the prior art, allows both the elongated member and the cable to simultaneously sit flush against the fractured bone. To this end, the cable is also able to stay in substantially direct contact with the outer circumference of the fractured bone section, unlike the prior art devices which create relatively large gaps between the cables and the bone. Flush mounting of the cable greatly reduces the risk of misalignment and improper healing of the bone. So, in this respect, the channeled bone plate disclosed herein provides superior support as an implant splint for the repair of severely fractured long bones.

In one embodiment, the transverse channel may include a pair of channels at opposite ends of the elongated member, or multiple transverse channels spaced intermittently along the length of the elongated member. Preferably, the transverse channel is of a size and shape to enclose the entire outer diameter of the cable, such as cables having between a 1.02-2.0 millimeter diameter. The shape of the transverse channel may include a concave arcuate indentation, such as a bell-curve shape, or a concave hemispherical indentation that intersects the bottom surface of the elongated member at a 90-degree angle. A fillet may be included between the transverse channel and the bottom surface to smooth or round out the transition between the channel and the bottom surface of the elongated member.

The elongated member may also include one or more apertures sized to accommodate selective insertion of one or more screws for securing the elongated member to the broken bone. Here, the screws may be at least flush with the top surface of the elongated member when fully inserted therein and exert a downward pressure thereon to force the bottom surface into flush engagement with the broken bone about the cable in the transverse channel. The elongated member may also optionally have one or more scallops cut into or formed from the edges of the top and/or bottom surfaces to reduce surface-to-surface interference between the elongated member and the blood vessels in the bone. The scallops may include depressions or indentations in the bottom surface or top surface, and may further aid in the healing process. In one embodiment, each scallop may be at least 50% of the width of the elongated member.

One method for implanting a channeled bone plate, as disclosed herein, includes placing a substantially rigid and elongated member having at least one transverse channel formed in a bottom surface thereof along an outer surface of fractured sections of a broken bone. Additionally, at least one cable is wrapped around the outer surface of the fractured sections of the broken bone. The cable is aligned with the elongated member for at least partial insertion of the cable into the transverse channel to permit flush mounting of the bottom surface of the elongated member to the outer surface of the fractured sections of the broken bone simultaneously with flush wrapping of the cable around the outer surface of the fractured sections of the broken bone. The elongated member is secured to the fractured sections of the broken bone, wherein the elongated member and the cable cooperate to support the broken bone as an implant splint.

A screw may be inserted into an aperture in the elongated member, wherein the screw exerts a downward pressure thereon to force the bottom surface into flush engagement with the outer surface of the fractured sections of the broken bone about the cable in the transverse channel. Of course, the method may further include the step of tightening the screw in the aperture and/or tightening the cable, especially when the cable is initially loosely wrapped around the outer surface of the fractured sections of the broken bone. In this respect, the placing step may occur after the wrapping step, wherein the aligning step includes the step of sliding the cable along the length of the broken bone. Alternatively, the wrapping step may include sliding the cable through the transverse channel when the elongated member is first at least partially secured to the broken bone. Preferably, the fractured sections of the broken bone are aligned and may be clamped together to help stabilize the fracture when implanting the splint.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 13 is a side view illustrating a pair of cables or wires securely holding sections of the fractured bone of FIG. 12 in alignment;

FIG. 14 is a side view similar to FIGS. 12-13, illustrating implanting a channeled bone plate over the cables or wires;

FIG. 15 is a side view similar to FIGS. 12-14, illustrating the implanted channeled bone plate and wires or cables implanted flush with the surface of the fractured bone;

FIG. 16 is a cross-sectional view taken about the line 16-16 in FIG. 15, further illustrating flush mounting of the channeled bone plate and cables or wires to the surface of the fractured bone;

DETAILED DESCRIPTION OF THE PREFERRED EMBODIMENTS

Figure 1:
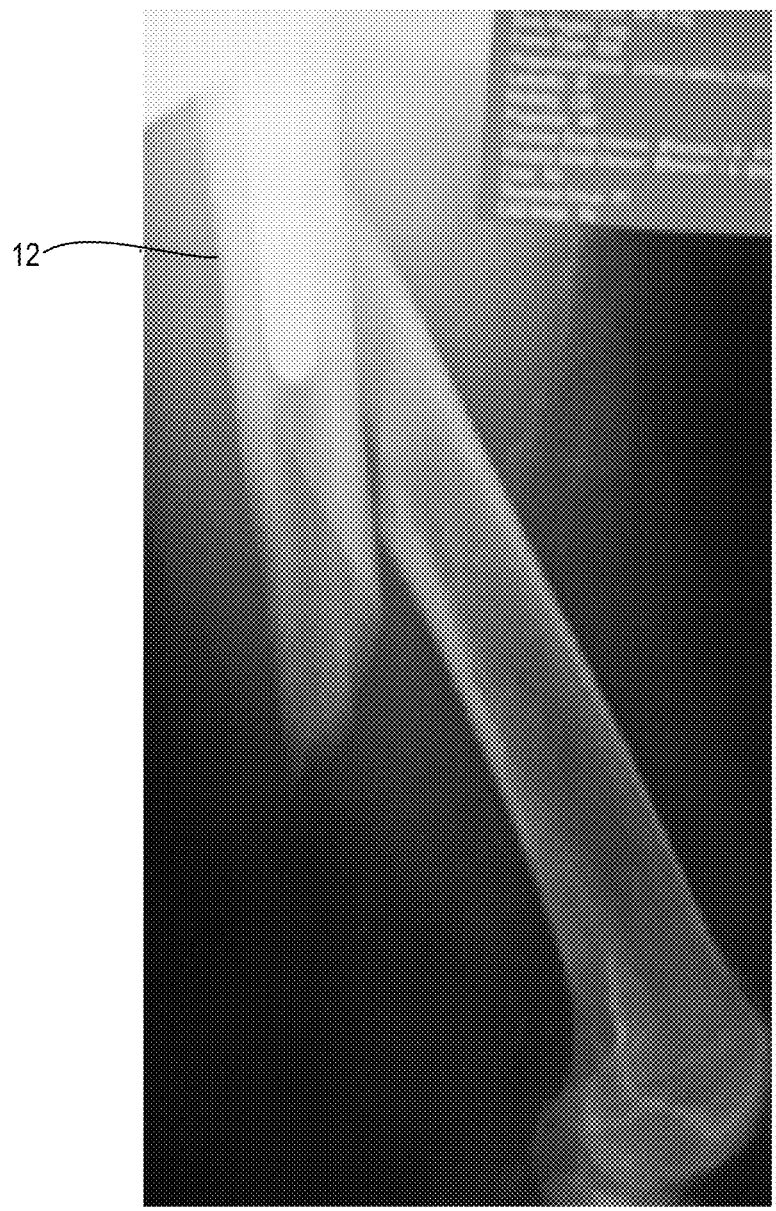
FIG. 1 illustrates a severe peri-prosthetic fracture of a femur.
Figure 5:
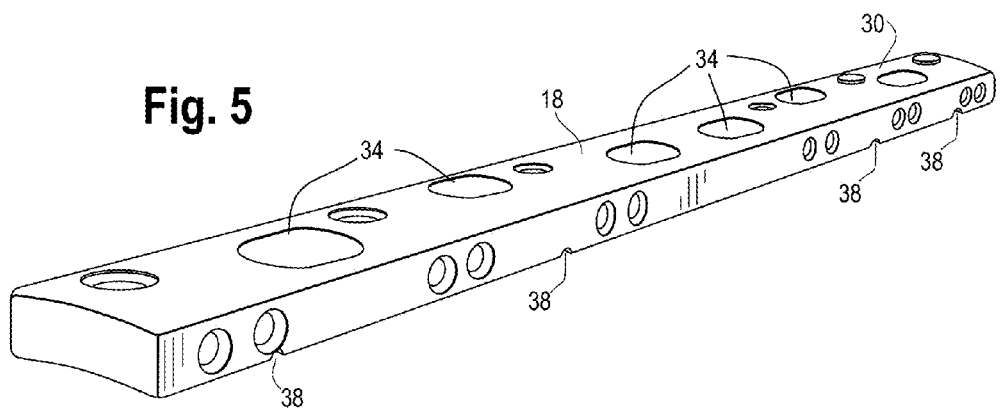
FIG. 5 is a perspective of a channeled bone plate as disclosed herein.
Figure 6:
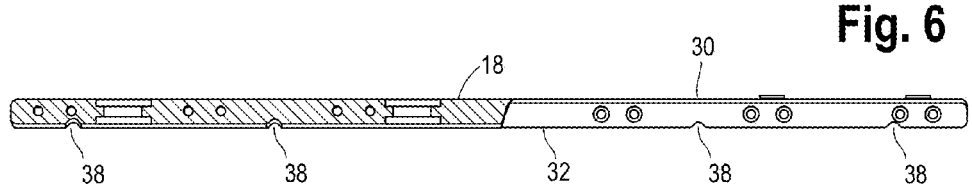
FIG. 6 is a partial cut-away side view of the channeled bone plate of FIG. 5.
Figure 7:
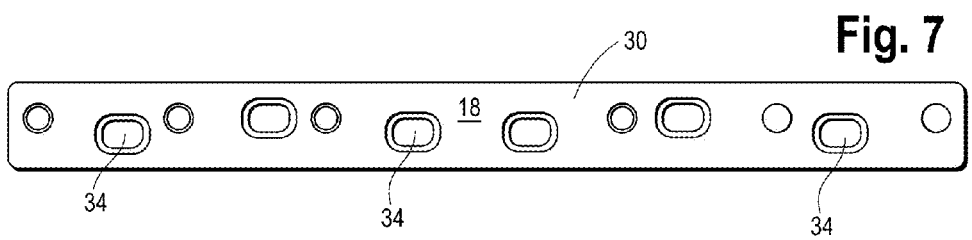
FIG. 7 is a top view of the channeled bone plate of FIG. 5, further illustrating a series of screw holes therein.
Figure 8:
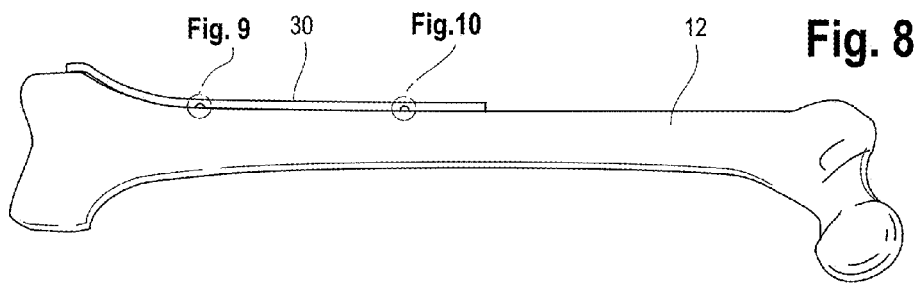
FIG. 8 is a side view similar to FIG. 6, further illustrating flush mounting of the channeled bone plate to a bone.

As shown in the drawings for purposes of illustration, the present invention for a channeled bone plate is shown generally by the reference numeral 30 in FIGS. 5-10, 14-15 and 18. The channeled bone plate 30 is a generally elongated and reinforced structure designed to provide support as a splint between fractured sections of bone, such as the periprosthetic fracture shown in FIG. 1. The channeled bone plate 30 is preferably rectangular, but may be any shape known in the art suitable for splinting sections of a fractured bone. In one embodiment, as shown in FIGS. 5 and 7, the channeled bone plate 30 may include a plurality of screw holes 34 that extend through the width of the plate 30. These screw holes 34 are of a size and shape to permit insertion of a screw 46 (e.g., as shown in FIG. 14) for purposes of screwing or securing the channeled bone plate 30 to fractured sections of the bone 12. In this respect, the screw head preferably sits flush or below the top surface 18 of the channeled bone plate 30 and exerts a generally downward pressure thereon to force the bottom surface 32 of the channeled bone plate 30 into flush engagement with the outer surface of the bone 12, as shown, e.g., in FIGS. 8, 14-15 and 18.

Figure 2:
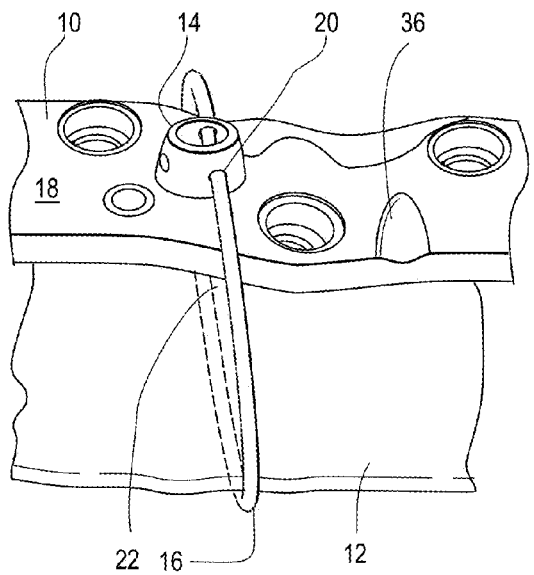
FIG. 2 is a perspective view of a prior art buttoned bone plate having a cable or wire coupled thereto and tied to a bone.

The bottom surface 32 of the channeled bone plate 30 may contain one or more scallops 36 (FIG. 2) to improve blood flow in and around the bone 12. The scallops 36 are indentations or depressions located along the outer edges the channeled bone plate 30 and improve blood flow in and around the surface of the bone 12 by offsetting the channeled bone plate 30 from the bone 12. That is, the relatively small space formed between the bone 12 and bottom surface 32 of the channeled bone plate 30 permits enhanced blood flow around this region. Adequate vascular pathways in and around the bone are important for controlling bone processes, such as osteochondral ossification. The scallops 36 are relatively wide (e.g., 50%-100% of the width of the channeled bone plate 30), but only extend across a small portion thereof (e.g., 30%). This allows the center of the channeled bone plate 30 to be in direct contact along the entire length of the bone 12. Incorporation of the scallops 36 advantageously results in the channeled bone plate 30 interfering with fewer blood vessels in the bone 12, thereby improving blood flow and aiding the healing process. Preferably, the scallops 36 only extend across part of the width of the channeled bone plate 30 (e.g., 30% as mentioned above), so the channeled bone plate 30 maintains adequate direct contact with the bone 12 for purposes of providing splinting support. Otherwise, the channeled bone plate 30 may not sufficiently brace the bone 12, which may lead to misalignment during the healing process. Of course, the scallops 36 may be of any shape, size or configuration (e.g., extending across the width or length of the channeled bone plate 30), so long as there is sufficient direct contact between the channeled bone plate 30 and the bone 12 to properly support fractured sections of the bone 12. The channeled bone plate 30 may include any number of scallops 36 on the top surface 18, the bottom surface 32, or a combination of the top and bottom surfaces 18 and 32. But, it is not necessary for the channeled bone plate 30 to include any scallops 36.

Figure 9:
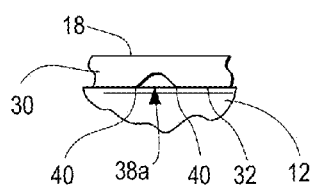
FIG. 9 is an enlarged side view taken about the circle 9 in FIG. 8, further illustrating a filleted channel.
Figure 10:
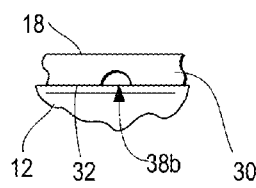
FIG. 10 is an enlarged side view taken about the circle 10 in FIG. 8, further illustrating a hemispherical channel.

The bottom surface 32 of the channeled bone plate 30 includes one or more channels 38 that extend across part or the entire width of the bottom surface 32 as best shown in FIGS. 5-6, and 8-10. The channel 38 is an indentation or hollowed out space having a size and shape to accommodate partial or full reception of the cables 16. In one embodiment, the channel 38 is a concave arcuate indentation having the general structure of a bell-curve 38a, as shown in FIG. 9. In an alternative embodiment, the channel 38 may define a more rigid arcuate channel that includes a concave hemispherical indentation or cut-out 38b as shown in FIG. 10. The bell-curve channel 38a provides a smoother transition to the bottom surface 32, such as by way of a fillet 40, while the hemispherical channel 38b forms harsher, near 90 degree intersection with the bottom surface 32. The former bell-curve channel 38a may be preferred for installation of the channeled bone plate 30 after the cables 16 are wrapped around fractured sections of the bone 12, as described in more detail below with respect to the method shown in FIG. 11. Alternatively, the latter hemispherical channel 38b is preferably used in association with the method shown and described in more detail below with respect to FIG. 17, as this channel 38b may more securely retain the cable 16 therein as the hemispherical cut-out more closely fits the exterior diameter of the cable 16.

In one embodiment, the channeled bone plate 30 may include a single bell-curve channel 38a. Although, more preferably, the channeled boned plate 30 includes at least two bell-curve channels 38a at opposing ends of the channeled bone plate 30 for holding together opposite sides of a fractured bone. Of course, the channeled bone plate 30 may include any number of the bell-curve channels 38a as may be needed to provide adequate splinting of fractured sections of the bone 12. Likewise, the channeled bone plate 30 may include a single hemispherical channel 38b, at least two hemispherical channels 38b at opposing ends of the channeled bone plate 30, or multiple hemispherical channels 38b intermittently spaced along the length of the channeled bone plate 30, as may be needed to provide adequate splinting of fractured sections of the bone 12. In another embodiment, the channeled bone plate 30 may include a combination of the bell-curve channels 38a and the hemispherical channels 38b. Here, the bell-curve channels 38a and the hemispherical channels 38b may alternate along the length of the channeled bone plate 30. Of course, the channeled bone plate 30 could include various combinations of the channels 38a, 38b, depending on the specific needs of the surgery. In general, for example, FIGS. 5-6 illustrate an embodiment wherein the channeled bone plate 30 includes four of the channels 38 and FIGS. 8 and 14-15 and 18 illustrate another embodiment wherein the channeled bone plate 30 includes two of the channels 38. In another alternative embodiment, the bell-curve channels 38a and/or the hemispherical channels 38b may be combined together or alone with other variously shaped channels 38 designed to accommodate reception and retainment of one or more cables 16. In this respect, the cables 16 and/or the channels 38 may be virtually any shape known in the art.

Importantly, the channel 38 should be of a size and shape that fully accommodates slide-fit reception of the cable 16 when wrapped around fractured sections of the bone 12 (e.g., as shown in FIGS. 14-15 and 19). The cables 16 are preferably 1.02 millimeters to 2.0 millimeters in diameter. Although, the cables 16 may be any diameter known in the art capable for use in combination with the channeled bone plate 30 to repair a bone fracture. For example, to accommodate the cable 16, the channel 38 is preferably a substantially elongated channel (i.e., longer than it is wide) formed transverse to the elongated channeled bone plate 30. Although, the channel 38 may be any size that allows the channeled bone plate 30 to fit flush against the bone 12. Narrower channels 38 advantageously increase direct contact between the channeled bone plate 30 and the bone 12, thereby increasing support. Although, if the width of the channel 38 is too small, i.e. smaller than the diameter of the cable 16, the cable 16 may not adequately fit into the channel 38 and the channeled bone plate 30 may not mount flush with the bone 12, thereby decreasing the overall support provided by an implanted channeled bone plate 30. Therefore, for the channeled bone plate 30 to provide maximum support, the channel 38 should be narrow enough to allow sufficient direct contact between the channeled bone plate 30 and the bone 12 to adequately brace the bone 12, yet be wide enough to fully accommodate the cable 16 so both the channeled bone plate 30 and the cable 16 are flush with the bone 12 after implantation.

Figure 3:
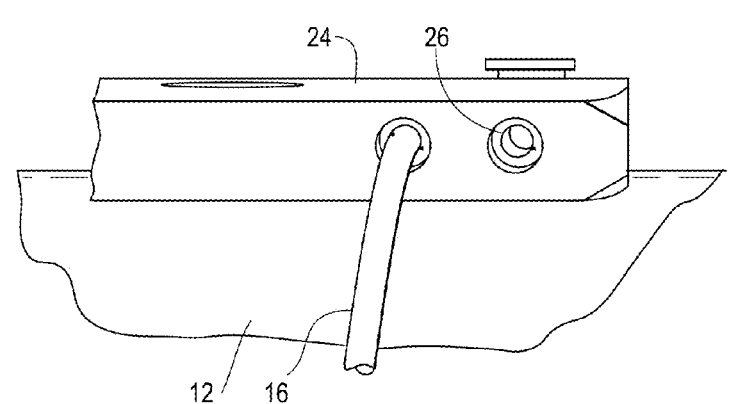
FIG. 3 is a side view of a prior art tunneled bone plate, illustrating fixation to a bone via a cable or wire extending therethrough.
Figure 4:
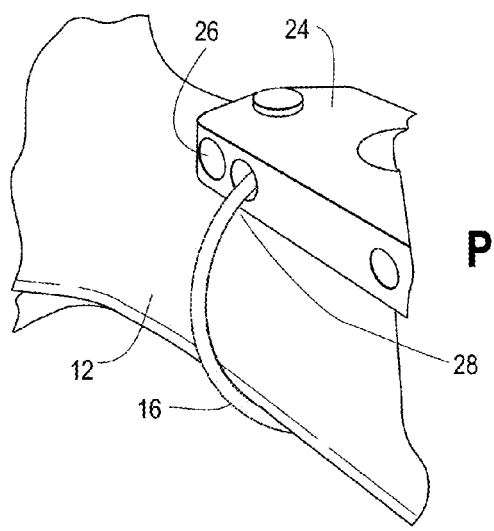
FIG. 4 is an alternative perspective view of the prior art tunneled bone plate of FIG. 3.

The channels 38 are notably different than and advantageous over the buttons 14 used with the buttoned bone plate 10 (FIG. 2) and the tunnels 26 used with the tunneled bone plate 24 (FIGS. 3 and 4) because the channeled bone plate 30 is able to sit flush over the cables 16, thereby surrounding the exterior surface of the cables 16 (i.e., the portion of the cable 16 not sitting flush against the surface of the bone 12), which eliminates the undesirable gaps 22 or 28 created as a result of implanting the buttoned bone plate 10 or the tunneled bone plate 24. That is, mounting the cable 16 to a portion of the bone plate biases the cable 16 away from the surface of the bone 12, thereby preventing full flush mounting. The channeled bone plate 30 advantageously provides increased direct surface area contact with the bone 12, as compared to the buttoned bone plate 10 and/or the tunneled bone plate 24. Since there is a portion of the buttoned bone plate 10 or the tunneled bone plate 24 between the cable 16 and the bone 12, the buttons 14 or the tunnels 26 prevent direct contact between the cable 16 and the outer circumference of the bone 12. Accordingly, the channels 38 in the channeled bone plate 30 eliminate the undesirable gaps 22, 28 to allow the full circumference of the bone 12 to optimally be in direct contact with the cable 16. Therefore, the channeled bone plate 30 provides more support to the bone 12 than the buttoned bone plate 10 or the tunneled bone plate 24. The surface area contact between the channeled bone plate 30 and the bone 12 lost because of the channels 38 is relatively negligible when compared to the buttoned bone plate 10 and the tunneled bone plate 24, for purposes of providing support in splinting fractured sections of the bone 12. In fact, wrapping the cables 16 directly around the bone 12 and mounting the channeled bone plate 30 flush with the bone 12 provides enhanced support relative to the bone plates 10, 24.

Figure 18:
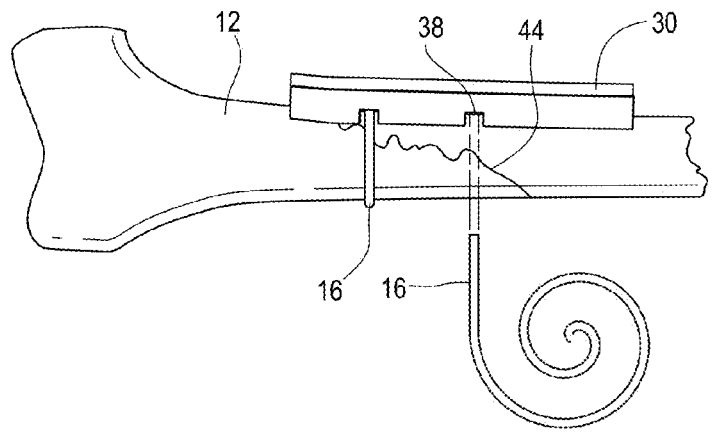
FIG. 18 is a side view similar to FIGS. 12-15, illustrating implanting the wires or cables after implanting the channeled bone plate.

More specifically, the channeled bone plate 30 is able to achieve greater support than the prior art because the channeled bone 30 plate allows both the cable 16 and the channeled bone plate 30 to be in their respective optimal positions, i.e., the channeled bone plate 30 and the cables 16 both sit flush with the surface of the bone 12, thereby supporting the bone 12 to the greatest possible extent. The cable 16 is wrapped tightly around the bone 12 without the relatively large gaps (numerals 22 and 28 in FIGS. 2 and 4, respectively) created by the buttoned bone plate 10 and the tunneled bone plate 24. When in this position, the cable 16 provides the most support for the bone 12. Similarly, the bone plate provides the most support when in direct contact with the bone 12 (e.g., as shown in FIGS. 14-15 and 18). The channels 38 allow the channeled bone plate 30 to be in direct contact with the bone 12 unlike the prior art where a non-channeled bone plate is implanted on top of the cables 16, thereby creating large gaps between the bone plate 10 or 24 and the bone 12. Therefore, even though the amount of direct contact between the channeled bone plate 30 and the bone 12 is somewhat reduced by the channels 38, the support provided by the channeled bone plate 30 is increased since the channeled bone plate 30 and the cables 16 are in their ideal positions.

Figure 11:
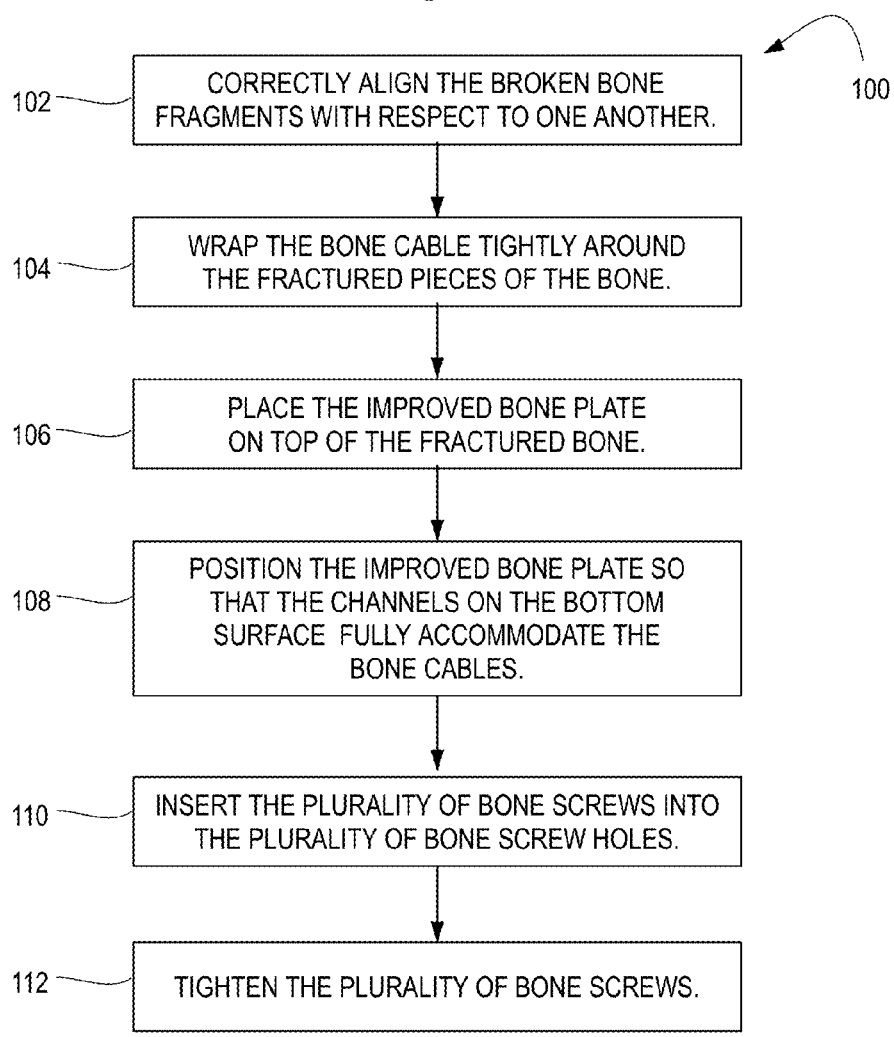
FIG. 11 is a flow chart illustrating a method for implanting the channeled bone plate over already implanted cables or wires wrapped around fractured sections of bone.
Figure 12:
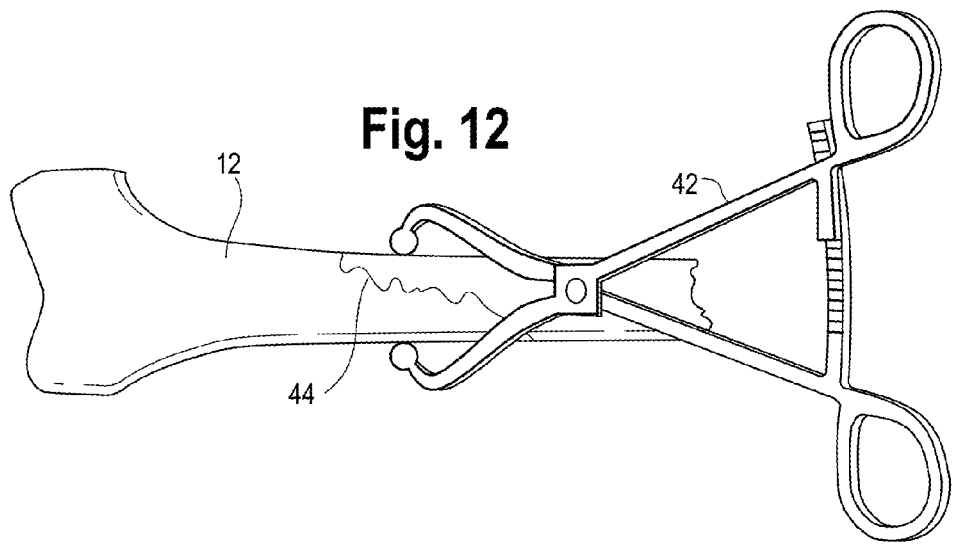
FIG. 12 is a side view of a fractured bone set with a clamp.

With respect to the methods disclosed herein, FIG. 11 illustrates one method (100) for implanting the channeled bone plate 30 after implanting the cables 16. The steps of this method (100) are more specifically shown and described below with respect to FIGS. 12-16. In this respect, the first step is to correctly align the broken bone fragments with respect to one another (102). This is typically accomplished with a clamp 42 (FIG. 12) or other pliers-like device or surgical tool that squeezes the fragments of the bone 12 back into proper alignment. For example, FIG. 12 illustrates the clamp 42 holding fragments of the bone 12 such that a fracture line 44 is visible when the fractured sections of the bone 12 are in proper alignment and ready for implantation of the channeled bone plate 30 and/or the cable(s) 16.

As shown in FIG. 11, the next step is to wrap one or more of the cables 16 around the fractured portions of the bone 12 in and around the fracture line 44 (FIG. 12) in accordance with step (104). In this embodiment, the cables 16 hold the fractured pieces of the bone 12 in proper alignment before implanting the channeled bone plate 30, and to facilitate healing. Preferably, the cables 16 wrap tight and flush to the surface of the bone 12 in the manner generally shown best in the cross-sectional view of FIG. 16. This, in turn, minimizes and preferably eliminates any gaps between the bone 12 and the cables 16, as are existent with the buttoned bone plate 10 and the tunneled bone plate 24, to the extent the gaps can be eliminated since the bone 12 may not be perfectly cylindrical. Importantly, however, these gaps are substantially relatively smaller than the gap 22 (FIG. 2) and the gap 28 (FIG. 4) created by the prior art bone plates 10 and 24 by way of bone plate material interference. During step (104), the cables 16 may be initially wrapped loosely around the bone 12, thereby allowing the cables 16 to slide longitudinally along the length of the bone 12 for purposes of alignment. Once the cables 16 are positioned as desired, the cables 16 are pulled tight to hold the fractured sections of the bone 12 together so the clamp 42 may be removed without the fractured sections separating. In other words, the cables 16 preferably maintain the bone 12 in the position generally shown in FIG. 12, without losing the fracture line 44. Accordingly, FIG. 13 shows the bone 12 after implantation of the cables 16 and removal of the clamp 42.

The next step as shown in FIG. 11 is to place the channeled bone plate 30 over the fractured portion of the bone 12 in accordance with step (106). The channeled bone plate 30 is aligned with the already wrapped cables 16 for insertion into respective channels 38 formed from the bottom surface 32 of the channeled bone plate 30, in accordance with step (108). The channels 38 allow the channeled bone plate 30 to sit flush against the bone 12, as described above. As shown in FIG. 14, and in accordance with steps (110) and (112) in FIG. 11, once the channeled bone plate 30 is correctly aligned with the cables 16, one or more screws 46 are inserted into respective screw holes 34 (FIGS. 5 and 7) to secure the channeled bone plate 30 to the bone 12. FIG. 15 illustrates the bone 12 after implantation of both the channeled bone plate 30 and cables 16. Furthermore, as illustrated in FIG. 16, the channeled bone plate 30, unlike the prior art bone plates 10 and 24 described above, permits flush mounting of the cables 16 to the exterior surface of the bone 12.

Figure 17:
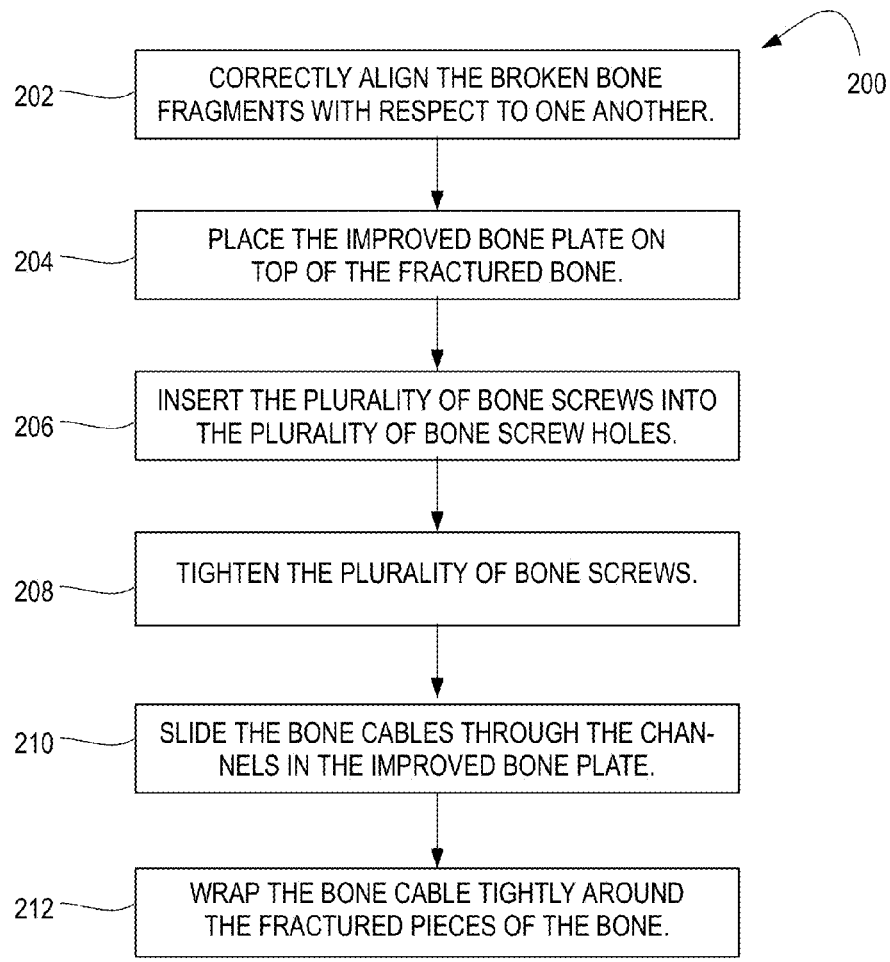
FIG. 17 is a flow chart illustrating an alternative method of implanting the channeled bone plate prior to implanting the wires or cables.

FIG. 17 is an alternative flow chart illustrating another method (200) for implanting the channeled bone plate 30 prior to implanting the cables 16. Here, the first step (202) is to align fractured sections of the bone 12 using the clamp 42, similar to step (102) described above with respect to FIGS. 11 and 12. The next step is to place the channeled bone plate 30 on top of the bone 12, in accordance with step (204). The position of the channeled bone plate 30 may be adjusted until the channels 38 (FIGS. 5-6 and 8-10) are positioned where the cables 16 are intended to be implanted.

In this method (200), the next step is to insert the bone screws 46 into the screw holes 34 and secure the channeled bone plate 30 to the bone 12, similar to the step described above with respect to step (110) in FIG. 11, and as shown in FIG. 14. The screws 46 may then be tightened (208) to more fully secure the channeled bone plate 30 to the bone 12. The next step is to slide a cable 16 through each respective channel 38 in accordance with step (210) in FIG. 17, and as illustrated in FIG. 18. This step is different than the method (100) as it requires threading the cable 16 through a channel 38 in the already implanted and screw mounted channeled bone plate 30. To this end, FIG. 15 illustrates the channeled bone plate 30 after implantation of both the channeled bone plate 30 and the cables 16. Similarly, FIG. 16 illustrates the flush mounting between the cable 16 and the bone 12 via the channels 38 (FIGS. 5-6 and 8-10) in the channeled bone plate 30.

Although several embodiments have been described in detail for purposes of illustration, various modifications may be made without departing from the scope and spirit of the invention. Accordingly, the invention is not to be limited, except as by the appended claims.

What is claimed is:

1. A method for implanting a channeled bone plate, comprising the steps of:

placing a substantially rigid and elongated member having at least one transverse channel formed in a bottom surface thereof along an outer surface of fractured sections of a broken bone;

wrapping at least one cable around the outer surface of the fractured sections of the broken bone;

aligning the cable with the elongated member for at least partial insertion of the cable into the at least one transverse channel to permit flush mounting of the bottom surface of the elongated member to the outer surface of the fractured sections of the broken bone simultaneously with flush wrapping of the cable around the outer surface of the fractured sections of the broken bone; and securing the elongated member to the fractured sections of the broken bone, wherein the elongated member and the cable cooperate to support the broken bone as an implant splint.

2. The method of claim 1, including the step of inserting a screw into at least one aperture in the elongated member, wherein the screw exerts a downward pressure thereon to force the bottom surface into flush engagement with the outer surface of the fractured sections of the broken bone about the at least one cable in the at least one transverse channel.

3. The method of claim 2, including the step of tightening the screw in the at least one aperture in the elongated member.

4. The method of claim 1, including the steps of aligning the fractured sections of the broken bone and clamping the fractured sections of the broken bone.

5. The method of claim 1, wherein the wrapping step includes the step of sliding the at least one cable through the at least one transverse channel.

6. The method of claim 1, wherein the placing step occurs after wrapping step.

7. The method of claim 6, wherein the aligning step includes the step of sliding the at least one cable along the length of the broken bone.

8. The method of claim 7, including the step of tightening the at least one cable initially loosely wrapped around the outer surface of the fractured sections of the broken bone.

* * * * *